United States Patent [19]

Eckhardt et al.

[11] 4,214,005

[45] Jul. 22, 1980

[54] FUNGICIDAL ALKOXYALKOXYACETYL ACYLALANINES

[75] Inventors: Wolfgang Eckhardt, Lörrach, Fed. Rep. of Germany; Adolf Hubele, Magden; Walter Kunz, Oberwil, both of Switzerland

[73] Assignee: Ciba-Geigy Corporation, Ardsley, N.Y.

[21] Appl. No.: 41,847

[22] Filed: May 24, 1979

[30] Foreign Application Priority Data

Jun. 2, 1978 [CH] Switzerland .......................... 6076/78

[51] Int. Cl.² .................... A61K 31/24; C07C 101/447
[52] U.S. Cl. ......................................... 424/309; 560/43
[58] Field of Search ........................... 560/43; 424/309

[56] References Cited

U.S. PATENT DOCUMENTS

| 4,032,657 | 6/1977 | Moser | 560/43 |
| 4,151,299 | 4/1979 | Hubele | 560/43 |

FOREIGN PATENT DOCUMENTS 2515091 10/1975 Fed. Rep. of Germany ............. 560/43

Primary Examiner—G. T. Breitenstein
Attorney, Agent, or Firm—Harry Falber

[57] ABSTRACT

Compounds of the formula I

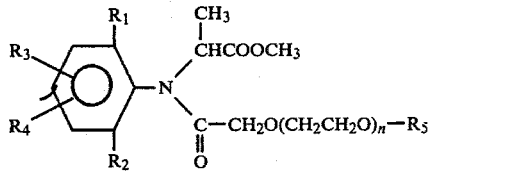

wherein
  $R_1$ represents $C_1$-$C_4$alkyl, $C_1$-$C_4$alkoxy or halogen,
  $R_2$ represents $C_1$-$C_3$alkyl, $C_1$-$C_4$alkoxy or halogen,
  $R_3$ represents hydrogen, $C_1$-$C_3$alkyl, $C_1$-$C_4$alkoxy or halogen,
  $R_4$ represents hydrogen or methyl,
  $R_5$ represents $C_1$-$C_4$alkyl or phenyl, and
  n is 1, 2 or 3. These compounds possess fungicidal action.

14 Claims, No Drawings

FUNGICIDAL ALKOXYALKOXYACETYL ACYLALANINES

The present invention provides compounds of the formula I

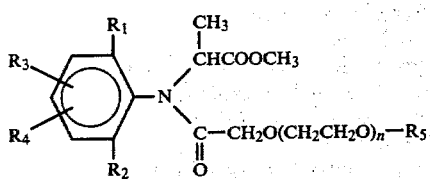

wherein
$R_1$ represents $C_1$-$C_4$alkyl, $C_1$-$C_4$alkoxy or halogen,
$R_2$ represents $C_1$-$C_3$alkyl, $C_1$-$C_4$alkoxy or halogen,
$R_3$ represents hydrogen, $C_1$-$C_3$alkyl, $C_1$-$C_4$alkoxy or halogen,
$R_4$ represents hydrogen or methyl,
$R_5$ represents $C_1$-$C_4$alkyl or phenyl, and
n is 1, 2 or 3,
processes for the manufacture of said compounds and compositions which contain them as active ingredients, and a method of protecting plants against attack by fungi which comprises the use of these compounds.

Depending on the stated number of carbon atoms, alkyl or the alkyl moiety of an alkoxy group denotes methyl, ethyl, propyl, isopropyl, butyl, isobutyl, sec-butyl or tert-butyl. Halogen is fluorine, chlorine, bromine or iodine.

The compounds of the formula I can be obtained by
(A) acylating a compound of the formula II

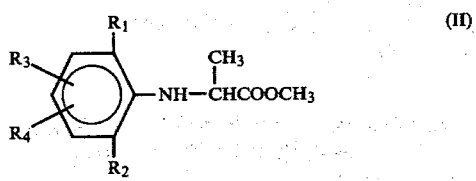

with a compound of the formula III $$HOOCCH_2O(CH_2-CH_2O)_n-R_5 \qquad (III)$$

or with a reactive derivative thereof, such as the acid halide or anhydride, or
(B) reacting an already acylated compound of the formula IV

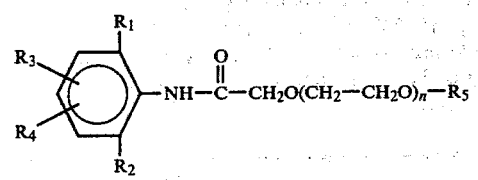

with a compound of the formula V

in the presence of a proton acceptor, such as butyl lithium or sodium hydride.

In the formulae II to V above, $R_1$ to $R_5$ and n are as defined for formula I, whilst Hal represents halogen, preferably chlorine or bromine.

The reactions may be carried out in the presence or absence of solvents or diluents which are inert to the reactants. Examples of suitable solvents or diluents are: aliphatic or aromatic hydrocarbons, such as benzene, toluene, xylenes, petroleum ether; halogenated hydrocarbons, such as chlorobenzene, methylene chloride, ethylene chloride, chloroform; ethers and ethereal compounds, such as dialkyl ethers, tert-butylmethyl ether, dioxane, tetrahydrofurane; nitriles, such as acetonitrile; N,N-dialkylated amides, such as dimethyl formamide, dimethyl sulfoxide, and mixtures of such solvents.

For the acylation according to process (A) it is possible to use the corresponding carboxylic acids themselves and, for example, their esters, but advantageously the acid anhydrides or the acid halides, preferably the acid chlorides or acid bromides.

The reaction temperatures are in the range between 0° C. and 180° C., preferably between 20° and 150° C. It is often advantageous to use acid acceptors or condensation agents. Suitable acid acceptors are tertiary amines, such as trialkylamines (e.g. triethylamine), pyridine and pyridine bases, or inorganic bases, such as the oxides and hydroxides, bicarbonates and carbonates of alkali metals and alkaline earth metals, and sodium acetate.

Process A, in which the starting materials are compounds of the formula II, can also be carried out without an acid acceptor, but in some cases it is expedient to introduce nitrogen in order to expel hydrogen halide. In other cases it is very advantageous to add dimethyl formamide as reaction catalyst.

The compounds of the formulae II to V are obtained by methods analogous to known ones.

The compounds of the formula I and the corresponding starting materials of the formulae II and V possess one centre of asymmetry (*)

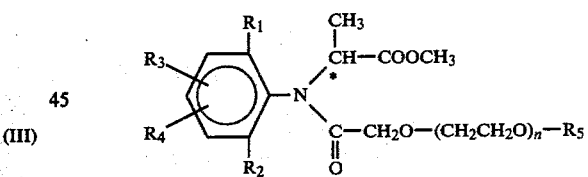

and can be separated into optical antipodes in conventional manner (e.g. fractional crystallisation or separation by chromatography). The different configurations of the formula I vary in the potency of their microbicidal action. The influence of further possible centres of asymmetry in the molecule and the atropisomerism about the phenyl -N< axis have little effect on the microbicidal action of the entire molecule. Provided no synthesis with the object of isolating pure isomers of the formula I or of their primary products is carried out, a product will normally be obtained as a mixture of isomers. Unless otherwise stated, throughout this specification a compound of the formula I is always to be understood as meaning a mixture of the different isomers.

German Offenlegungsschrift 2 515 091 discloses similar acyl anilines as microbicides, compared with which the compounds of the present invention have certain advantages.

The compounds of the formula I possess for practical purposes a very advantageous fungicidal spectrum for protecting cultivated plants without damage to these being caused by undesirable side effects. Examples of cultivated plants within the scope of this invention are: cereals, maize, rice, vegetables, sugar-beet, soya beans, ground nuts, fruit trees, ornamentals, and, in particular, vines, hops, cucumber plants (cucumber, marrows, melons), solanaceae, such as potatoes, tobacco plants and tomatoes, and also banana, cocoa and natural rubber plants.

With the active compounds of the formula I it is possible to inhibit or destroy the fungi which occur in plants or parts of plants (fruit, blossoms, leaves, stems, tubers, roots) in these and also related crops of useful plants, and also to protect from attack by such fungi the parts of plants which grow later. The active compounds are effective against phytopathogenic fungi which belong to the following classes: Ascomycetes (e.g. Erysiphaceae); Basidiomycetes, in particular rust fungi; fungi imperfecti (e.g. Moniliales); and especially against the Oomycetes belonging to the class of the Phycomycetes, such as Phytophthora, Peronospora, Pseudoperonosphora, Pythium or Plasmopara. In addition, the compounds of the formula I possess a systemic action. They can also be used as seed dressing agents for protecting seeds (fruit, tubers, grains) and plant cuttings from fungus infections and from phytopathogenic fungi which occur in the soil.

Preferred fungicides are compounds of the formula I, wherein $R_1$ represents methyl, $R_2$ represents methyl, ethyl, chlorine or bromine, $R_3$ represents hydrogen, halogen or methyl, and $R_4$ represents hydrogen or methyl, and $R_5$ and n are as defined for formula I.

An interesting group of compounds is that wherein $R_5$ in formula I represents methyl, n is preferably 1.

Combinations of the above groups of compounds are also to be understood as being preferred. Among the very highly active compounds, the compound designated hereinafter as compound 2 is to be singled out and is accordingly a preferred individual compound within the scope of the present invention.

An interesting individual group of compounds comprises compounds of the formula I, wherein $R_1$ represents methyl, $R_2$ represents methyl or chlorine, $R_3$ represents hydrogen, methyl, chlorine or bromine, $R_4$ represents hydrogen or methyl, n is 1 or 2 and $R_5$ represents $C_1$-$C_4$alkyl, in particular methyl or n-butyl.

The compounds of the formula I can be used by themselves or together with suitable carriers and/or other adjuvants. Suitable carriers and adjuvants can be solid or liquid and correspond to the substances normally used in the art of formulation, for example natural or regenerated mineral substances, solvents, dispersants, wetting agents, tackifiers, thickeners, binders or fertilisers.

The content of active substance in commercial compositions is between 0.1% and 90% by weight.

For application, the compounds of the formula I may be processed to the following formulations (in which the bracketed weight percentages refer to advantageous amounts of active ingredient):

Solid formulations:
dusts, tracking agents, (up to 10%) granules (coated granules, impregnated granules and homogeneous granules); pellets (1 to 80%);

Liquid formulations:
(a) active substance concentrates which are dispersible in water: wettable powders, pastes; (25–90% in commercial packs, 0.01 to 15% in ready for use solutions emulsions; concentrated solutions (10 to 50%; 0.01 to 15% in ready for use solutions).
(b) Solutions (0.1 to 20%); aerosols.

It will be readily understood that the compounds of the formula I can be used together with other known fungicides and also with suitable insecticides, acaricides, nematicides, herbicides, fertilisers etc., in order to broaden the activity spectrum of the formulations.

The invention is illustrated by the following Examples, but without any restriction to what is described therein.

MANUFACTURING EXAMPLE

Example 1

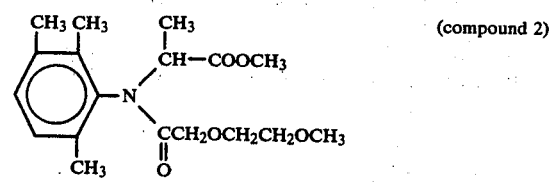

(compound 2)

N-(1'-methoxycarbonylethyl)-N-(2'-methoxyethoxyacetyl)-2,3,6-trimethylaniline 11.1 g (0.05 mole) of N-(1'-methoxycarbonylethyl)-2,3,6-trimethylaniline are dissolved in 80 ml of toluene. A solution of 15.2 g (0.1 mole) of 2'-methoxyethoxyacetyl chloride in 20 ml of toluene is then added dropwise at room temperature to the above solution. The reaction mixture is refluxed for 16 hours and the HCl gas which evolves is expelled with nitrogen. After cooling, the toluene solution is washed in succession with 1 N sodium hydroxide solution and water, dried over sodium sulfate, filtered and concentrated in a water jet vacuum. The residual oil yields 8.9 g of product with a boiling point of 154°–160° C./0.1 torr.

The following compounds of the formula I can be obtained in analogous manner or by one of the methods described herein.

| Compound | $R_1$ | $R_2$ | $R_3$ | $R_4$ | n | $R_5$ | Physical data |
|---|---|---|---|---|---|---|---|
| 1 | $CH_3$ | $CH_3$ | H | H | 1 | $CH_3$ | b.p. 152°–155° C. /0.15 torr |
| 2 | $CH_3$ | $CH_3$ | 3-$CH_3$ | H | 1 | $CH_3$ | b.p. 154°–160° C. /0.1 torr |
| 3 | $CH_3$ | $CH_3$ | 3-$CH_3$ | 5-$CH_3$ | 1 | $CH_3$ | b.p. 155°–158° C. /0.1 torr |

-continued

| Compound | R$_1$ | R$_2$ | R$_3$ | R$_4$ | n | R$_5$ | Physical data |
|---|---|---|---|---|---|---|---|
| 4 | CH$_3$ | Cl | H | H | 1 | CH$_3$ | b.p. 160°–168° C. /0.15 torr |
| 5 | CH$_3$ | CH$_3$ | 3-Cl | H | 1 | CH$_3$ | b.p. 161°–166° C. /0.2 torr |
| 6 | CH$_3$ | CH$_3$ | 4-Br | H | 1 | CH$_3$ | b.p. 178°–183° C. /0.2 torr |
| 7 | CH$_3$ | CH$_3$ | 4-Cl | H | 1 | CH$_3$ | |
| 8 | CH$_3$ | OCH$_3$ | H | H | 1 | CH$_3$ | |
| 9 | CH$_3$ | CH$_3$ | H | H | 1 | C$_2$H$_5$ | |
| 10 | CH$_3$ | CH$_3$ | 3-CH$_3$ | H | 1 | C$_2$H$_5$ | |
| 11 | CH$_3$ | CH$_3$ | 3-CH$_3$ | 5-CH$_3$ | 1 | C$_2$H$_5$ | |
| 12 | CH$_3$ | CH$_3$ | H | H | 1 | C$_4$H$_9$(n) | |
| 13 | CH$_3$ | CH$_3$ | 4-Cl | H | 1 | C$_4$H$_9$(n) | |
| 14 | CH$_3$ | CH$_3$ | H | H | 2 | CH$_3$ | n$_D^{21}$ 1.5130 |
| 15 | CH$_3$ | CH$_3$ | 3-CH$_3$ | H | 2 | CH$_3$ | n$_D^{21}$ 1.5170 |
| 16 | CH$_3$ | CH$_3$ | 3-CH$_3$ | 5-CH$_3$ | 2 | CH$_3$ | oil |
| 17 | CH$_3$ | CH$_3$ | H | H | 2 | C$_2$H$_5$ | |
| 18 | CH$_3$ | CH$_3$ | 3-CH$_3$ | H | 2 | C$_2$H$_5$ | |
| 19 | CH$_3$ | CH$_3$ | H | H | 3 | C$_2$H$_5$ | |
| 20 | CH$_3$ | CH$_3$ | 3-CH$_3$ | 5-CH$_3$ | 3 | C$_2$H$_5$ | |
| 21 | CH$_3$ | CH$_3$ | H | H | 3 | C$_4$H$_9$(n) | |
| 22 | CH$_3$ | CH$_3$ | 4-Cl | H | 3 | C$_4$H$_9$(n) | |
| 23 | CH$_3$ | CH$_3$ | H | H | 1 | C$_6$H$_5$— | |
| 24 | CH$_3$ | CH$_3$ | 3-CH$_3$ | H | 1 | C$_6$H$_5$— | |
| 25 | CH$_3$ | CH$_3$ | 3-CH$_3$ | 5-CH$_3$ | 1 | C$_6$H$_5$— | |
| 26 | CH$_3$ | CH$_3$ | H | H | 2 | C$_4$H$_9$(n) | n$_D^{21}$ 1.6898 |

BIOLOGICAL EXAMPLES

EXAMPLE 2

Action against Pythium debaryanum on sugar beets

The fungus was cultivated on sterile oat grains and added to a mixture of earth and sand. Flower pots were filled with the infected soil in which sugar beet seeds were then sown. Immediately after sowing, the test preparations formulated as wettable powders were poured in the form of aqueous suspensions over the soil (20 ppm of active substance, based on the volume of the soil). The pots were then stood for 2–3 weeks in a greenhouse at 20°–24° C. The soil was kept uniformly moist by gently spraying it with water. The emergence of the sugar beet plants as well as the number of healthy and sick plants were determined in evaluating the texts.

EXAMPLE 3

Action against Phytophthora infestans on tomatoes (a) Curative Action

"Roter Gnom" tomato plants were sprayed when 3 weeks old with a zoospore suspension of the fungus and incubated in a climatic chamber at 18° to 20° C. and saturated humidity. The humidifying was interrupted after 24 hours. After the plants had dried, they were sprayed with a broth containing the active substance formulated as a wettable powder in a concentration of 0.06%. After the spray coating had dried, the plants were again kept in the humid chamber for 4 days. The effectiveness of the tested substances was assessed by determining the size and number of the typical leaf specks which had occurred during this time.

(b) Preventive-systemic action

The active substance formulated as a wettable powder was applied in a concentration of 0.006% (based on the volume of the soil) to the surface of the soil of 3-week-old "Roter Gnom" tomatoes in pots. Three days later the underside of the leaves of the plants was sprayed with a zoospore suspension of Phytophthora infestans. The plants were then kept in a spray chamber at 18° to 20° C. and saturated humidity for 5 days, after which time typical leaf specks formed. The effectiveness of the tested substance was accessed by determining the size and number of the specks.

EXAMPLE 4

Action against Plasmopara viticola (Bert. et Curt.) (Berl. et de Toni) on vines (a) Residual preventive action Vine cuttings of the variety "Chasselas" were reared in a greenhouse. Three plants in the 10 leaf stage were sprayed with a broth (containing 0.06% of active substance) prepared from the active substance and formulated as a wettable powder. After the coating layer had dried, the plants were infected on the underside of the leaves with the spore suspension of the fungus. The plants were subsequently kept in a humid chamber for 8 days, after which time symptoms of the disease were visible on the control plants. The effectiveness of the tested substance was assessed by determining the number and size of the infected areas on the treated plants.

(b) Curative action

Vine cuttings of the variety "Chasselas" were reared in a greenhouse and infected in the 10 leaf stage on the underside of the leaves with a spore suspension of Plasmopara viticola. After they had been kept for 24 hours in a humid chamber, the plants were sprayed with a 0.06% broth prepared from the active substance formulated as wettable powder. The plants were then kept in a humid chamber for a further 7 days, after which time the symptoms of the disease were visible on the control plants. The effectiveness of the tested substances was accessed by determining the size and number of the infected areas.

The compounds of the formula I exhibited a good fungicidal action in one or more of these tests. For example, the compounds listed below inhibited attack by the following fungi to less than 20% in comparison with infected control plants (100% attack):
Pythium debaryanum: compounds 1, 2, 3, 4 and 5
Phytophthora infestans: compounds 1, 2, 3, 4, 5, 6, 14, 15, 16 and 26
Plasmopara viticola: compounds 1, 3 and 5.

FORMULATION EXAMPLES

EXAMPLE 5

Dusts: The following substances are used to formulate (a) 5% and (b) a 2% dust:
(a)
5 parts of active substance
95 parts of talc;
(b)
2 parts of active substance
1 part of highly dispersed silicic acid
97 parts of talc.

The active substances were mixed with the carriers and ground and in this form can be processed to dusts for application.

EXAMPLE 6

Granulate: The following substances are used to formulate a 5% granulate:
5 parts of active substance
0.25 part of epichlorohydrin
0.25 part of cetyl polyglycol ether
3.25 parts of polyethylene glycol
91 parts of kaolin (particle size 0.3–0.8 mm).

The active substance is mixed with epichlorohydrin and the mixture is dissolved in 6 parts of acetone. Then polyethylene glycol and cetyl polyglycol ether are added. The resultant solution is sprayed on kaolin and the acetone is evaporated in vacuo. Such a microgranulate is advantageously used for combating soil fungi.

EXAMPLE 7

Wettable powders: The following constituents are used to formulate (a) a 70%, (b) a 40%, (c) and (d) a 25% and (e) a 10% wettable powder:
(a)
70 parts of active substance
5 parts of sodium dibutylnaphthylsulfonate
3 parts of naphthalenesulfonic acid/phenolsulfonic acid/formaldehyde condensate (3:2:1)
10 parts of kaolin
12 parts of Champagne chalk
(b)
40 parts of active substance
5 parts of sodium ligninsulfonate
1 part of sodium dibutylnaphthalenesulfonic acid
54 parts of silicic acid
(c)
25 parts of active substance
4.5 parts of calcium ligninsulfonate
1.9 parts of Champagne chalk/hydroxyethyl cellulose mixture (1:1)
1.5 parts of sodium dibutylnaphthalenesulfonate
19.5 parts of silicic acid
19.5 parts of Champagne chalk
28.1 parts of kaolin
(d)
25 parts of active substance
2.5 parts of isooctylphenoxy-polyethylene-ethanol
1.7 parts of a Champagne chalk/hydroxyethyl cellulose mixture (1:1)
8.3 parts of sodium aluminium silicate
16.5 parts of kieselguhr
46 parts of kaolin
(e)
10 parts of active substance
3 parts of a mixture of the sodium salts of saturated fatty alcohol sulfates
5 parts of naphthalenesulfonic acid/formaldehyde condensate
82 parts of kaolin.

The active substances are intimately mixed in suitable mixers with the additives and ground in appropriate mills and rollers. Wettable powders of excellent wettability and suspension power are obtained. These wettable powders can be dilured with water to give suspensions of the desired concentration and can be used in particular for leaf application.

EXAMPLE 8

Emulsifiable concentrates: The following substances are used to formulate a 25% emulsifiable concentrate:
25 parts of active substance
2.5 parts of epoxidised vegetable oil
10 parts of an alkylarylsulfonate/fatty alcohol polyglycol ether mixture
5 parts of dimethyl formamide
57.5 parts of xylene.

By diluting such a concentrate with water it is possible to prepare emulsions of the desired concentration, which are especially suitable for leaf application.

What is claimed is:

1. A compound of the formula

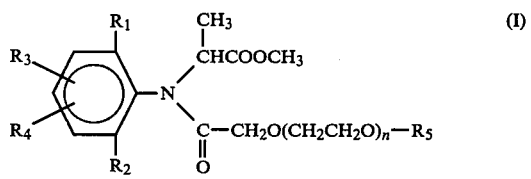

wherein
$R_1$ represents $C_1$–$C_4$alkyl, $C_1$–$C_4$alkoxy or halogen,
$R_2$ represents $C_1$–$C_3$alkyl, $C_1$–$C_4$alkoxy or halogen,
$R_3$ represents hydrogen, $C_1$–$C_3$alkyl, $C_1$–$C_4$alkoxy or halogen,
$R_4$ represents hydrogen or methyl,
$R_5$ represents $C_1$–$C_4$alkyl or phenyl, and
n is 1, 2 or 3.

2. A compound of the formula I according to claim 1, wherein $R_1$ represents methyl, $R_2$ represents methyl or chlorine, $R_3$ represents hydrogen, methyl, chlorine or bromine, $R_4$ represents hydrogen or methyl, $R_5$ represents $C_1$–$C_4$alkyl and n is 1 or 2.

3. A compound according to claim 1, wherein $R_1$ represents methyl, $R_2$ represents methyl, ethyl, chlorine or bromine, and $R_3$ represents hydrogen, methyl or halogen.

4. A compound according to any one of claims 1 to 3, wherein $R_5$ represents methyl.

5. A compound according to claim 1 wherein n is 1.
6. A compound according to claim 2 wherein n is 1.
7. A compound according to claim 3 wherein n is 1.
8. A compound according to claim 4 wherein n is 1.

9. A compound according to claim 2, wherein $R_5$ represents methyl or n-butyl.

10. N-(1'-Methoxycarbonylethyl)-N-(2'-methoxyethoxyacetyl)-2,3,6-trimethylaniline according to claim 8.

11. N-(1'-Methoxycarbonylethyl)-N-(2'-methoxyethoxyacetyl)-3-chloro-2,6-dimethylaniline according to claim 8.

12. A fungicidal composition containing, as active component, a fungicidally effective amount of at least one compound according to claim 1 together with a suitable carrier therefor.

13. A method for controlling fungi, which comprises applying to said fungi or their environment a fungicidally effective amount of a compound according to claim 1.

14. A method according to claim 13 wherein the fungi to be controlled are phytopathogenic.

* * * * *